United States Patent [19]

Davies et al.

[11] 4,179,653
[45] Dec. 18, 1979

[54] CORROSION MONITORING PROBE

[75] Inventors: Michael Davies; Glyn Hourihan; Frank Smith, all of Runcorn, England

[73] Assignee: Imperial Chemical Industries Limited, London, England

[21] Appl. No.: 880,305

[22] Filed: Feb. 22, 1978

[30] Foreign Application Priority Data

Mar. 3, 1977 [GB] United Kingdom ............... 9000/77

[51] Int. Cl.² .......................................... G01R 27/02
[52] U.S. Cl. ............................... 324/65 CR; 73/86; 324/71 E
[58] Field of Search ............ 324/65 CR, 71 E; 73/86; 23/230 C; 422/53; 304/195 C

[56] References Cited

U.S. PATENT DOCUMENTS

| | | | |
|---|---|---|---|
| 2,864,925 | 12/1958 | Ellison | 324/65 CR |
| 2,878,354 | 3/1959 | Ellison | 73/86 X |
| 2,982,930 | 5/1961 | Wygant | 324/65 CR |
| 3,060,728 | 10/1962 | Wolber | 324/65 CR |
| 3,156,887 | 11/1964 | Weikal | 324/65 CR |
| 3,228,236 | 1/1966 | Landrum et al. | 73/86 |
| 3,627,493 | 12/1971 | Manley | 73/86 X |
| 3,817,707 | 6/1974 | Cummings | 73/86 X |
| 3,910,830 | 10/1975 | Mayse | 73/86 X |

*Primary Examiner*—Stanley T. Krawczewicz
*Attorney, Agent, or Firm*—Cushman, Darby & Cushman

[57] ABSTRACT

A corrosion monitoring probe comprising a body member, preferably a tubular body member, a seal within the body member, and a metallic probe element which is contained in part within the body member and which in part projects beyond the seal, at least that part of the probe element which projects beyond the seal being corrodable, in which the seal is in the form of at least one gasket made of an electrically insulating compressible material and in which the probe is provided with means for compressing the gasket(s) to cause the gasket(s) to form a seal between the probe element and the body member.

12 Claims, 4 Drawing Figures

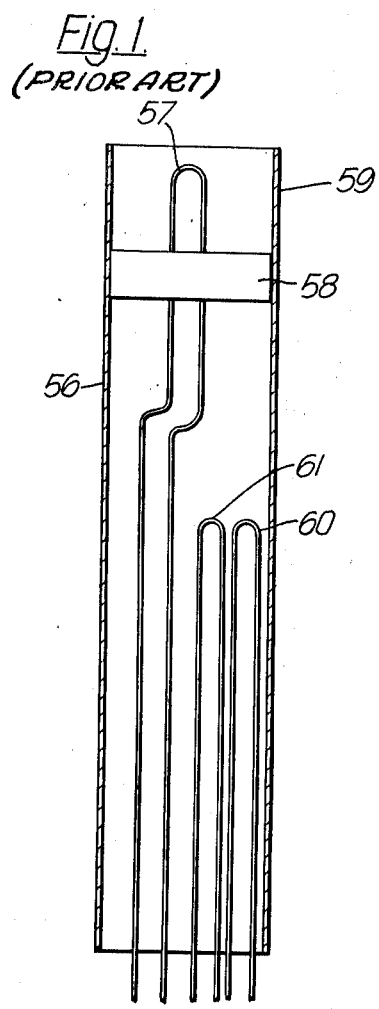
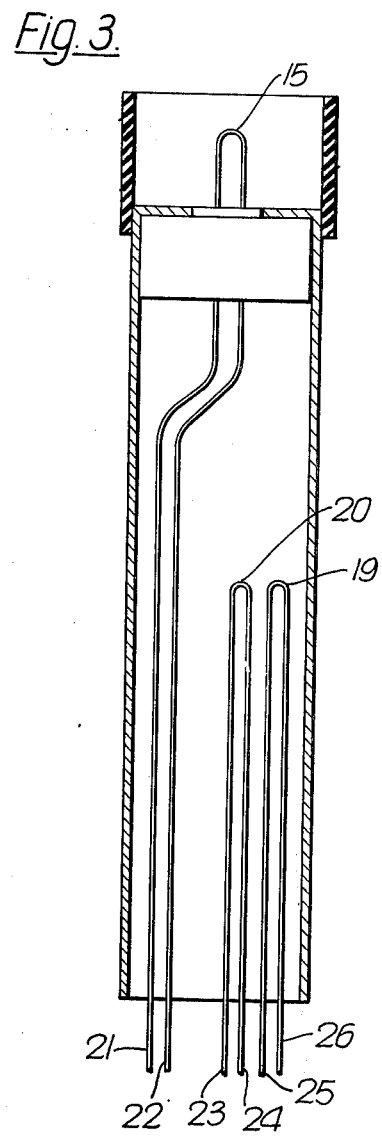

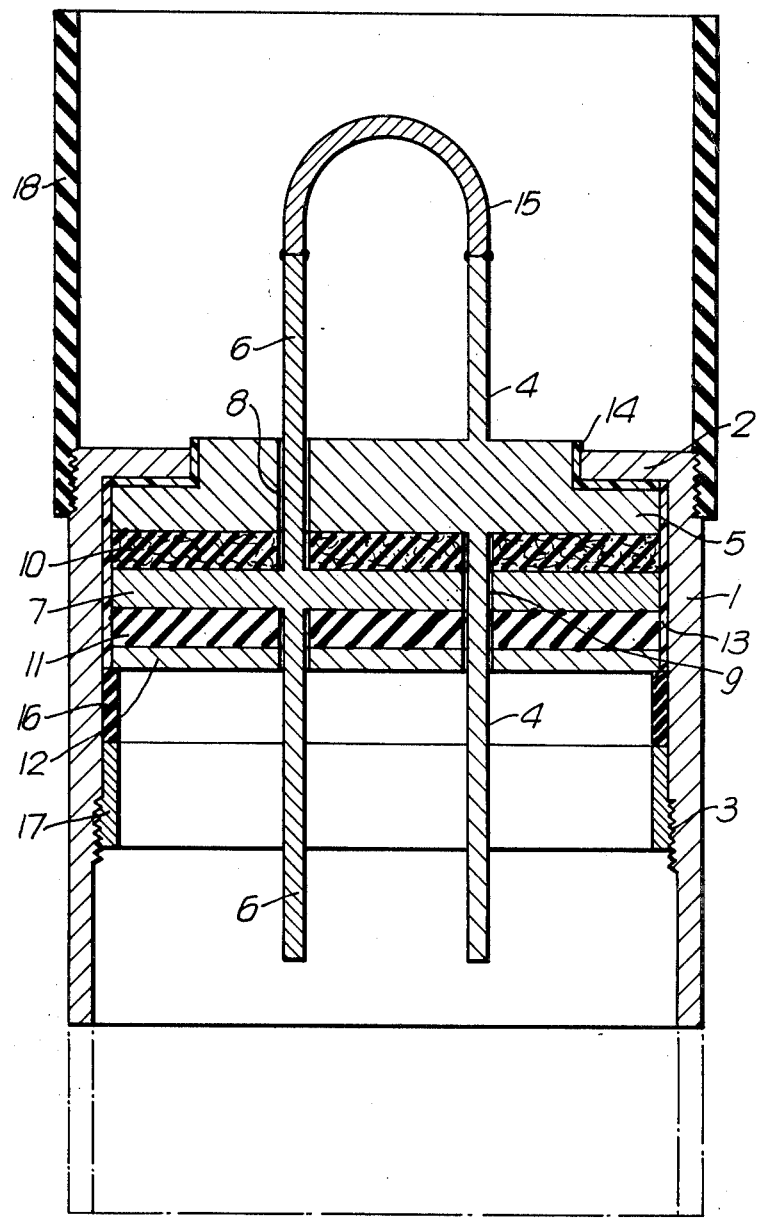

CORROSION MONITORING PROBE

BACKGROUND AND SUMMARY OF THE INVENTION

This invention relates to a corrosion monitoring probe.

It is desirable to be able to measure the rate at which a corrosive material corrodes equipment in which such a material is contained. For example, a chemical plant may be corroded by the reactants and/or by the product of reactions taking place in the plant and it is clearly desirable, by means of a suitable monitoring means, to be able to detect whether or not corrosion is taking place, and if so the rate of corrosion, so that remedial action may be taken before the extent of the corrosion becomes so great that failure of the plant occurs, possibly with catastrophic consequences. This is particularly important at regions of the plant which may be particularly prone to corrosion.

Corrosion monitoring probes are known which fulfil this function. For example, a probe is known which comprises a body member, generally of tubular shape, and a pair of electrodes which project from the body and which are sealed to the body at the end thereof by means of a seal of an electrically insulating material which may be, for example, a ceramic seal or an organic resin seal, e.g. an epoxy resin. The body of the probe may be inserted into the plant which contains the corrosive material with the electrodes projecting into the corrosive material. In order to measure the rate of corrosion of the electrodes a small potential (e.g. 20 mv) is applied across the electrodes to cause a small current to flow through the corrosive material. This current varies with the corrosion of the electrodes and measurement of the current may be used to obtain a measure of the rate of corrosion of the material of the electrodes. The probe may contain three electrodes, one being a reference electrode. This probe may only be used to measure the corrosion caused by electrically-conducting liquids.

The probe comprises a body member and a metallic probe element which is sealed to the body by means of a seal of an electrically insulating material which may be, for example a ceramic seal or an organic resin seal, e.g. an epoxy resin seal. The upper part of the probe element in the form of a continuous wire connecting the two arms of the probe element, which in use is corroded, projects from the seal and is protected from mechanical damage by an open-ended shield. The body may house a metallic check element and a metallic reference element which are protected from the corrosive material by means of the seal. The body may be equipped with means for securing it to the equipment which contains the corrosive material. For example, where the probe is to be used to monitor the corrosion in a chemical plant the body may be equipped with an external screw-thread by means of which it may be secured to the plant in a corresponding screw-threaded aperture in the plant, or it may be secured in an aperture in the plant by means of a gland.

In use, the probe element is corroded by the corrosive material and as the cross-sectional area of the element is decreased due to the corrosion the electrical resistance of the element increases. A measure of the corrosion taking place may be determined by measuring the resistance of the probe element at intervals of time and noting the change in resistance.

If the resistance of the probe element is measured directly the data obtained will be affected by the temperature of the element as well as by its cross-sectional area. In order to eliminate variations in the measured resistance due to variations in temperature the corrosion monitoring probe preferably also includes a reference element and optionally a check element. In use the resistance of the probe element is compared with the resistance of the reference element, which will be at the same temperature as the probe element, using a Wheatstone bridge arrangement. Before taking a measurement the resistance of the reference element may be checked against that of a check element to ensure that the resistance of the former element has not changed.

Corrosion monitoring probes of the aforementioned types suffer from a disadvantage in that during use the seal may be damaged, for example, by mechanical action and/or by chemical action of the corrosive material on the seal. The extent of the damage may be such that the corrosive material is allowed to pass the seal and penetrate into the body of the probe. The result of penetration of corrosive material into the body of the probe may be that incorrect readings of the current passing between the electrodes, or incorrect readings of the electrical resistance of the metallic probe element, may be obtained. Incorrect measures of the rate of corrosion will thus be obtained. In the case where the body of the probe contains a reference element, the corrosive material which penetrates into the body of the probe may attack the reference element and change its resistance so that when in use the resistance of the probe element is compared with that of a corrosion-affected reference element an incorrect measurement of the resistance of the probe element will be obtained.

We now provide a corrosion monitoring probe in which the possibility of corrosive material penetrating the body of the probe is at least much reduced, and may even be substantially eliminated.

The present invention provides a corrosion monitoring probe comprising a body member, a seal within the body member, and a metallic probe element which is contained in part within the body member and which in part projects beyond the seal, at least that part of the probe element which projects beyond the seal being corrodable, in which the seal is in the form of at least one gasket made of an electrically insulating compressible material and in which the probe is provided with means for compressing the gasket(s) to cause the gasket(s) to form a seal between the probe element and the body member.

The metallic probe element may be of the type comprising two or more electrodes in which corrosion of the probe element is determined by measuring the change which occurs with corrosion of the electrodes in the current which passes between the electrodes when a given small potential difference is applied across the electrodes.

Alternatively, the metallic probe element may be of the type comprising a continuous element in which corrosion of the probe element is determined by measuring the change in electrical resistance of the probe element which occurs with corrosion of the element.

Use of the former type is limited to corrosive materials which are liquid and which are electrically-conducting. The latter type may be used with such corrosive electrically-conducting liquid materials and in addition may be used with non-conducting corrosive liquid materials, for example, hydrocarbons, and with corrosive gaseous materials.

The probes may be fitted with means for connecting the probe element to suitable electrical equipment, in the case of the probe element comprising at least two electrodes to means for generating a potential difference across the electrodes and to means for measuring the resultant current, and in the case of the probe element comprising a continuous element to means for measuring the electrical resistance of the element. In the latter case the body of the corrosion monitoring probe may contain a reference element the resistance of which may be compared with that of the probe element using a Wheatstone bridge arrangement as hereinbefore described. The body of the probe may also contain a check element.

The probe element may be made of any desired metal the corrosion of which it is desired to determine. However, where the corrosion monitoring probe is to be used to measure corrosion in a chemical plant the probe element will generally be made of the same metal as that from which the plant is constructed, or at least of the same metal as that part of the plant where the probe is installed. The probe element may for example be made of mild steel, stainless steel or titanium.

The body member of the corrosion monitoring probe, which in general will be metallic and which is preferably made of a material which is not significantly corroded by the corrosive material, may be of tubular shape and suitably includes an annular lip on which an annular gasket may bear and against which a gasket may be compressed in order to effect a seal between the probe element and the body thereby preventing ingress of corrosive material into the body of the probe.

The means for compressing the gasket(s) may be an annular sleeve or sleeves positioned within the body member. The sleeve may be externally screw-threaded and it may be attached to the body member via a corresponding internal screw-thread on the body. The sleeve may bear directly, or indirectly, on the gasket(s), tightening of the sleeve causing the gasket(s) to be compressed thereby effecting a seal.

By a gasket we mean a packing member of any desired shape which is capable of being compressed. The gasket may be generally flat, e.g. in the form of a flat disc, in the form of a sleeve, or in the form of a ring, e.g. a so-called O-ring. The corrosion monitoring probe may contain more than one gasket and the number of gaskets used, and their precise type, will depend on the precise configuration of the body member and of the probe element of the corrosion monitoring probe. For example, in the probe a gasket may be compressed and caused to bear on both the body member and the probe element thereby effecting a seal. Alternatively, the probe may contain a plurality of gaskets and at least one non-compressible member between the body member and the probe element with at least one gasket being compressed and bearing on the probe element and on the non-compressible member or members and at least one gasket being compressed and bearing on the body member and the non-compressible member or members thereby effecting a seal.

The material of the gasket(s), which will be an electrically insulating material, should be selected bearing in mind the nature of the corrosive material with which the probe and gasket(s) come into contact. Clearly, a material will be selected for the gasket(s) which is resistant to corrosion by the corrosive material. Materials from which the gasket(s) may be constructed include, polytetrafluoroethylene (PTFE), natural rubber, a synthetic rubber, e.g. neoprene rubber, and compressed asbestos fibre (CAF).

A particular embodiment of a corrosion monitoring probe of the invention comprises:
 (a) a tubular body member having an annular lip at its upper end,
 (b) a probe element comprising at least two metallic discs each disc having a pin above and below the plane of the disc and a channel or channels through the disc, the discs being positioned one on top of the other so that the pins of a particular disc pass through the channels in the adjacent disc or discs,
 (c) a seal comprising a gasket or gaskets in the form of channelled disc(s) of an electrically insulating material positioned between adjacent metallic discs, and an annular gasket of an electrically insulating material positioned between the upper metallic disc and the lip of the body member, and
 (d) means for compressing the channelled disc(s) and the annular gasket so as to effect a seal.

At least part of the pins above the planes of the discs will be of a corrodable metal. If desired the pins and discs may be made in whole of a corrodable metal.

The means for compressing the seal may be a screw-threaded sleeve mounted on an internal screw thread on the body member. The screw-threaded sleeve should be insulated electrically from the discs of the probe element, e.g. by means of a disc of insulating material positioned below the bottom disc of the probe element.

The pins in the upper faces of the metallic discs may form the electrodes of a corrosion monitoring probe. Alternatively, the pins may be connected to form a corrodable continuous metallic element.

The probe element may comprise two metallic discs each disc having a pin above and below the plane of the disc and each disc having a channel through the plane of the disc to accommodate a pin of the other disc when the probe element is assembled in the corrosion monitoring probe. Thus, the pin on the lower face of the upper disc passes through the channel in the lower disc and the pin on the upper face of the lower disc passes through the channel in the upper disc.

The probe element may comprise three metallic discs each disc having a pin above and below the plane of the disc and each disc having two channels through the plane of the disc each channel accommodating a pin of the other discs when the probe element is assembled. The holes and pin in each disc will be symmetrically disposed on the face of each disc. The three pins in the probe element may function as corrodable electrodes in the corrosion monitoring probe.

In a further embodiment the probe element may comprise four metallic discs each disc having a pin above and below the plane of the disc and three channels through the plane of the disc each channel accommodating a pin of the other discs when the probe element is assembled. The holes and pin in each disc will be symmetrically disposed on the face of each disc. The four pins in the probe element may function as two pairs of corrodable electrodes. Alternatively, pairs of pins may be connected to form corrodable continuous metallic elements, or one pair of pins may serve as corrodable electrodes and one pair may be connected to form a corrodable continuous metallic element.

The pins may be provided with means for connection to suitable electrical equipment.

The seal may also include a sleeve of an electrically insulating material positioned in the annular space between the assembled metallic discs and discs of insulating material and the body member. Compression of the insulating discs causes them to bear on the sleeve and effect a seal with the body member.

It is the primary object of the present invention to provide an improved corrosion-monitoring probe.

BRIEF DESCRIPTION OF THE DRAWINGS

FIG. 1 is a diagrammatic representation of an exemplary prior art corrosion-monitoring probe;

FIG. 2 is a cross-sectional view of an exemplary-corrosion monitoring probe according to the present invention;

FIG. 3 is a diagrammatic representation of the probe of FIG. 2; and

DETAILED DESCRIPTION OF THE DRAWINGS

Figure 4:
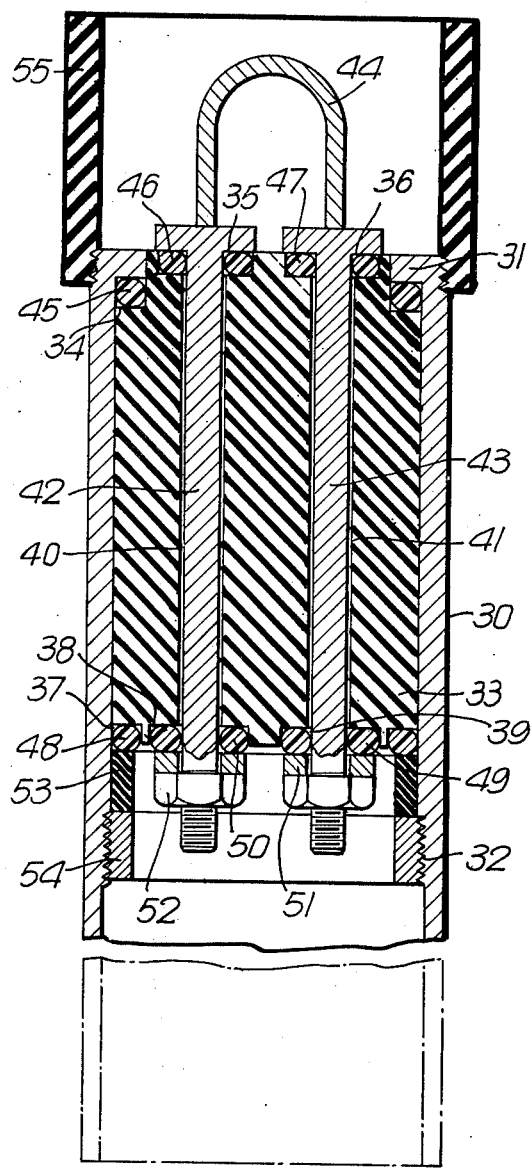
FIG. 4 is a cross-sectional view of another corrosion-monitoring probe.

The prior art probe of FIG. 1 includes a body number 56 and a metallic probe element 57 which is sealed to the body by means of a seal of an electrically insulating material 58. The upper part of the probe element is in the form of a continuous wire connecting the two arms of the probe element, which in use is corroded. The upper part of the probe element projects from the sealing and is protected from mechanical damage by an open ended shield 59. The body may house a metallic check element 60 and a metallic reference element 61 which are protected from the corrosive material by means of a seal. Although not shown in FIG. 1, the body may be equipped with means for securing it to the equipment which contains the corrosive material pass through the channel (9) and the upper part of the pin (6) may pass through the channel (8). The discs and pins are made of the metal whose corrosion is to be tested, in this embodiment mild steel. Between the discs (5 and 7) there is positioned a gasket (10) having channels to receive the pins (4, 6) and made of compressed asbestos fibre (C.A.F.). A similar channelled CAF disc (11) is positioned below the disc (7) and a channelled Inconel disc (12) is positioned below the CAF disc (11). The assembled Inconel and CAF discs are positioned within a PTFE sleeve (13) and a PTFE gasket (14) is positioned on the disc (5). The probe element is completed be a mild steel connecting piece (15) welded to the tops of the pins (4 and 6). (Alternatively, the connecting piece (15) may be omitted and the pins (4, 6) may form electrodes). The assembled Inconel and CAF discs are held in position in the body (1) by means of an Inconel sleeve (16), which is slotted into the body (1), and a screw-threaded Inconel sleeve (17), which cooperates with the screw thread (3) on the body (1). The upper part of the body (1) carries a screw-threaded sleeve (18) which serves to protect the probe element from mechanical damage. The body (1) may be provided with means (not shown) for securing the probe into a plant. For example, the body may carry an external screw thread by means of which the probe may be secured in a corresponding aperture in a plant. Alternatively, the body may be secured into a plant by means of a gland.

If desired the pins (4 and 6) may carry PTFE sleeves at least in the region where they pass through the channels (9 and 8) in order to ensure that there is no contact between the pin (4) and the second disc (7) and between the pin (6) and the first disc (5) which may result in an electrical short circuit.

In order to assemble the corrosion monitoring probe shown in FIG. 2 the mild steel discs (5 and 7) and their associated pins, the CAF discs (10 and 11), the Inconel disc (12), and the PTFE gasket (14) are fitted together, the thus formed assembly is inserted into the PTFE sleeve (13), and mild steel connecting piece (15) is welded to the tops of the pins (4 and 6). The assembly is then inserted into the body (1) with the gasket (14) bearing on the lip (2) of the body (1), the sleeve (16) and the screwthreaded sleeve (17) are inserted into the body, and the protective sleeve (18) is attached to the upper part of the body. Finally, the screw-threaded sleeve (17) is screwed tightly into the body (1) causing the PTFE gasket (14) to bear onto the lip (2) of the body (1) and to form a seal with the body, and causing CAF discs (10 and 11) to be compressed and to expand radially and bear on the PTFE sleeve (13) thereby forming a seal with the body (1).

The corrosion monitoring probe shown in FIG. 3 is a diagrammatic representation on a reduced scale of the probe shown in FIG. 2. In addition to those parts of the probe described with reference to FIG. 2 the probe shown in FIG. 3 comprises a reference element (19) and a check element (20), both made of mild steel and both housed within the body (1) of the probe. Also shown are the electrical leads (21 to 26) via which the probe element, the reference element, and the check element may be connected to a Wheatstone bridge measuring device in known manner.

In use the corrosion monitoring probe is inserted through a corresponding aperture into a plant, for example a chemical plant, for at least a distance sufficient for the probe element to be in contact with the corrosive material in the plant and for the elements which are housed within the body of the probe, and which are thus protected from corrosion by the material in the plant, to be at the same temperature as the probe element. The probe element and the reference and check elements are then connected to a Wheatstone bridge arrangement and the corrosion caused by the material in the plant is determined by comparing the resistance of the probe element with that of the reference element and noting the change in resistance of the probe element with time. Before a measurement of the resistance of the probe element is made the resistance of the reference element is compared with that of the check element to ensure that the resistance of reference element has not itself been affected, for example by corrosion. The various elements should all be at the same temperature so as to ensure that discrepancies caused by variation of resistance with temperature are eliminated.

If desired the reference and check elements (19 and 20) may be omitted and the resistance of the probe element may be measured directly to obtain a measure of the corrosion in the plant. However, as the resistance may change with change in temperature of the material in the plant as well as with the amount of corrosion of the probe element there will be some uncertainty in the corrosion data obtained. This uncertainty is eliminated if the resistance of a probe element is compared with that of a reference element which is at the same temperature as the probe element.

A further embodiment of a corrosion-monitoring probe of the invention comprises:

(a) a tubular body member having an annular lip at its upper end, (b) a probe element comprising a rod which is preferably of an electrically insulating material, for example of ceramic material or of a plastics material, preferably a filled plastics material, e.g. filled poly (tetrafluoroethylene), adapted to fit into the tubular body member, the rod having channels positioned lengthwise of the rod and at least two metallic pins, the pins being positioned in separate channels in the rod, (c) a seal comprising gaskets of an electrically insulating material between the pins and the rod and between the rod and the lip of the tubular body member, and (d) means for compressing the gaskets so as to effect a seal.

The gasket positioned between the rod and the body member may be an annular gasket positioned between the upper face of the rod and the lip of the body member. The means for compressing this gasket may be a screw-threaded sleeve mounted on an internal screw thread on the body member and bearing on the rod.

The pins at one end may each have an annular lip and at the other end may be screw-threaded. The gaskets between the pins and the channelled rod may be annular gaskets positioned between the lips of the pins and the rod and the means for compressing the gaskets may be nuts on the screw-threaded ends of the pins which may bear on the rod.

The corrosion monitoring probe may comprise two pins. The pins may form the electrodes of a corrosion monitoring probe or they may be connected to form a continuous corrodable metallic element. In alternative embodiments the probe may comprise three pins each forming an electrode, or the probe may comprise four pins in which case the pins may function as two pairs of corrodable electrodes, or pairs of pins may be connected to form two corrodable continuous metallic elements, or one pair of pins may serve as corrodable electrodes and one pair may be connected to form a corrodable continuous element.

A particular embodiment of the corrosion monitoring probe of the type broadly described above will now be described with the aid of FIG. 4.

The corrosion monitoring probe shown in FIG. 4 is a cross-sectional view in elevation. The probe comprises a tubular body (30) made of Inconel having an annular lip (31) and a screw thread (32). A probe assembly is housed within the body. The probe assembly comprises a rod (33) of insulating material (e.g. a ceramic material) having three annular channels (34, 35, 36) at its upper end, three annular channels (37, 38, 39) at its lower end, and two channels (40, 41) passing lengthwise through the rod. The pins (42, 43) are positioned in the channels (40, 41) the pins at their upper ends having annular lips and at their lower ends being screw-threaded. The pins are made of mild steel. A mild steel connecting piece (44) is welded to the upper end of the pins (42, 43) to complete the probe element. Neoprene rubber O-rings (45, 46, 47) are positioned in the channels (34, 35, 36) at the upper end of the ceramic rod and at the lower end of the ceramic rod neoprene rubber O-rings (48, 49, 50) are positioned in the channels (37, 38, 39). The pins (42, 43) are held in position in the rod by means of washers (51) and screw-threaded nuts (52) with the lips at the upper ends of the pins bearing on the O-rings (46, 47). The rod is held in position in the tubular body by means of an Inconel sleeve (53) and a screw-threaded sleeve (54) with the O-ring (45) bearing on the lip (31) of the body (30) and the sleeve (53) bearing on the O-ring (48). The upper part of the tubular body carries a screw-threaded sleeve (55) which serves to protect the probe element from mechanical damage. The tubular body (30) is provided with means (not shown) for securing the probe into a plant, e.g. a chemical plant. For example, the body may carry an external screw thread by means of which the probe may be secured in a corresponding aperture in a plant. Alternatively, the corrosion monitoring probe may be secured in a plant by means of a gland.

In order to assemble the corrosion monitoring probe shown in FIG. 4 the O-rings (45, 46, 47) are inserted in the channels (34, 35, 36), the O-rings (48, 49, 50) are inserted in the channels (37, 38, 39), the pins (42, 43) are inserted through the channels (40, 41), and the washers (51) and nuts (52) are attached to the lower ends of the pins. The nuts are tightened up to cause the O-rings (46, 47, 49, 50) to be compressed in their respective channels thus sealing off the channels (40, 41) from ingress by corrosive material from the plant into which the corrosion monitoring probe is inserted. The connecting piece (44) is then welded to the upper ends of the pins (42, 43). Alternatively, the connecting piece may be welded to the pins before the pins are inserted through channels in the ceramic rod. The rod and its associated pins is then placed into the tubular body (30), and the sleeve (53) and screw-threaded sleeve (54) are inserted. The screw-threaded sleeve (54) is tightened up to cause the O-rings (45, 48) to be compressed in their respective channels thus sealing off the annular space between the tubular body (30) and the ceramic rod (33) from ingress by corrosive material from the plant into which the corrosion monitoring prone is inserted. Finally, the screw-threaded sleeve (55) is attached to the upper part of the tubular body (30).

The corrosion monitoring probe described with reference to FIG. 4 may also be provided with a reference element and a check element housed within the body of the probe in a manner similar to that described with reference to the probe of FIG. 3. Also, the probe may be provided with electrical leads in the manner described with reference to FIG. 3.

The corrosion monitoring probe may be used in a manner as hereinbefore described.

What we claim is:

1. A corrosion monitoring probe comprising
   an elongated tubular body member having an annular lip at an upper end thereof;
   a probe element comprising at least two metallic discs, each disc having a pin above and below the plane of the disc and at least one channel through the disc, the discs being positioned one on top of the other so that the pins of a particular disc pass through a channel in an adjacent disc;
   a seal comprising at least one gasket in the form of a channelled disc of an electrically insulating material, positioned between adjacent metallic discs, and an annular gasket of an electrically insulating material positioned between the upper metallic disc and the lip of the body member; and
   means for compressing the channelled disc and the annular gasket so as to effect a seal.

2. A probe as recited in claim 1 wherein said means for compressing said channelled disc and annular gasket comprises a screw-threaded sleeve positioned in the body member and insulated electrically from the probe element.

3. A probe as recited in claim 1 which comprises two metallic discs, each disc having a pin above and below the plane of the disc.

4. A probe as recited in claim 1 which comprises four metallic discs each disc having a pin above and below the plane of the disc and three channels through the plane of the disc to accommodate a pin of each of the other discs.

5. A probe as recited in claim 4 wherein one pair of pins serve as a pair of corrodable electrodes and one pair of pins are connected to form a continuous corrodable metallic element.

6. A probe as recited in claim 1 further comprising a sleeve of an electrically insulating material positioned in the annular space between the body member and the assembled metallic discs and discs of insulating material.

7. A probe as in claim 1 wherein said probe element is selected from the group consisting essentially of mild steel, stainless steel, and titanium.

8. A probe as recited in claim 1 wherein said body member contains a reference element.

9. A probe as recited in claim 1 wherein said means for compressing said gasket comprises an annular sleeve positioned within said body member.

10. A probe as recited in claim 1 wherein said gasket is selected from the group consisting essentially of polytetrafluoroethylene, natural rubber, synthetic rubber and compressed asbestos fibre.

11. A probe as recited in claim 1 wherein said body member contains a check element.

12. A probe as recited in claim 1 wherein a pair of pins are connected to form a continuous corrodable metallic element.

* * * * *